(12) United States Patent
Klug et al.

(10) Patent No.: US 10,172,774 B2
(45) Date of Patent: Jan. 8, 2019

(54) USE OF N-METHYL-N-ACYLGLUCAMINES AS THICKENING AGENTS IN SURFACTANT SOLUTIONS

(71) Applicants: Peter Klug, Grossostheim (DE); Carina Mildner, Frankfurt am Main (DE)

(72) Inventors: Peter Klug, Grossostheim (DE); Carina Mildner, Frankfurt am Main (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/401,789

(22) PCT Filed: May 29, 2013

(86) PCT No.: PCT/EP2013/061100
§ 371 (c)(1),
(2) Date: Nov. 17, 2014

(87) PCT Pub. No.: WO2013/178697
PCT Pub. Date: Dec. 5, 2013

(65) Prior Publication Data
US 2015/0126616 A1 May 7, 2015

(30) Foreign Application Priority Data

May 30, 2012 (DE) .......... 10 2012 010 652
May 6, 2013 (DE) .......... 10 2013 208 258

(51) Int. Cl.
| | | |
|---|---|---|
| A61K 8/42 | (2006.01) | |
| A61Q 19/10 | (2006.01) | |
| A61K 8/60 | (2006.01) | |
| A61Q 5/02 | (2006.01) | |
| A61K 8/46 | (2006.01) | |
| A61K 8/44 | (2006.01) | |

(52) U.S. Cl.
CPC .......... *A61K 8/42* (2013.01); *A61K 8/44* (2013.01); *A61K 8/442* (2013.01); *A61K 8/463* (2013.01); *A61K 8/60* (2013.01); *A61Q 5/02* (2013.01); *A61Q 19/10* (2013.01); *A61K 2800/48* (2013.01); *A61K 2800/596* (2013.01)

(58) Field of Classification Search
None
See application file for complete search history.

(56) References Cited

U.S. PATENT DOCUMENTS

| | | | |
|---|---|---|---|
| 5,009,814 A | 4/1991 | Kelkenberg et al. | |
| 5,354,425 A * | 10/1994 | Mackey | D21H 23/50 162/111 |
| 5,716,922 A * | 2/1998 | Curry | C11D 1/652 134/25.2 |
| 6,274,126 B1 * | 8/2001 | Newell | A61K 8/22 424/62 |
| 6,887,838 B2 * | 5/2005 | Dykstra | C07D 223/16 510/303 |
| 2001/0023298 A1 | 9/2001 | Weinelt | |
| 2009/0023622 A1 | 1/2009 | Leidreiter et al. | |
| 2015/0125415 A1 | 5/2015 | Klug et al. | |
| 2015/0126424 A1 | 5/2015 | Klug et al. | |
| 2015/0133560 A1 | 5/2015 | Klug et al. | |
| 2015/0140048 A1 | 5/2015 | Klug et al. | |
| 2015/0141466 A1 | 5/2015 | Klug et al. | |
| 2015/0141508 A1 | 5/2015 | Klug et al. | |
| 2015/0150767 A1 | 6/2015 | Klug et al. | |
| 2015/0164755 A1 | 6/2015 | Klug et al. | |
| 2015/0164756 A1 | 6/2015 | Klug et al. | |
| 2015/0320037 A1 | 11/2015 | Wacker | |
| 2016/0074310 A1 | 3/2016 | Klug et al. | |
| 2016/0136072 A1 | 5/2016 | Klug et al. | |
| 2016/0143828 A1 | 5/2016 | Klug et al. | |
| 2016/0243014 A1 | 8/2016 | Dahms et al. | |
| 2016/0272666 A1 | 9/2016 | Klug et al. | |
| 2016/0361243 A1 | 12/2016 | Klug et al. | |
| 2017/0000710 A1 | 1/2017 | Klug et al. | |
| 2017/0002297 A1 | 1/2017 | Klug et al. | |
| 2017/0044434 A1 | 2/2017 | Baur et al. | |
| 2017/0055524 A1 | 3/2017 | Baur et al. | |
| 2017/0071199 A1 | 3/2017 | Baur et al. | |
| 2017/0101606 A1 | 4/2017 | Klug et al. | |
| 2017/0218293 A1 | 8/2017 | Klug et al. | |
| 2017/0265477 A1 | 9/2017 | Baur et al. | |
| 2017/0292062 A1 | 10/2017 | Wylde et al. | |
| 2017/0305838 A1 | 10/2017 | Appel et al. | |

FOREIGN PATENT DOCUMENTS

| | | |
|---|---|---|
| EP | 0 285 768 | 10/1988 |
| EP | 0 550 637 | 7/1993 |
| JP | S63270534 A | 11/1988 |
| JP | H11505839 A | 5/1995 |
| WO | WO 92/06158 | 4/1992 |
| WO | WO 92/06162 | 4/1992 |
| WO | WO-1992-06162 * | 4/1992 |
| WO | WO 93/18125 | 9/1993 |
| WO | WO 94/12608 | 6/1994 |
| WO | WO 95/17880 | 7/1995 |
| WO | WO 96/10386 | 4/1996 |
| WO | 96/37589 A1 | 11/1996 |

OTHER PUBLICATIONS

U.S. Appl. No. 14/401,315, now published as US 2015-0133560.
(Continued)

Primary Examiner — Jianfeng Song
(74) Attorney, Agent, or Firm — Tod A. Waldrop

(57) ABSTRACT

N-methyl-N-acylglucamines are suitable as thickening agents in aqueous surfactant solutions containing one or more anionic surfactants of the group including alkyl ether sulfates and alkyl sulfates, the N-methyl-N-acylglucamines containing at least 60 wt.-% of N-methyl-N-acylglucamines that have a $C_{12}$-, $C_{14}$-acyl group or an unsaturated $C_{18}$-acyl group and at the same time less than 5 wt.-% of N-methyl-N-acylglucamines that contain an acyl group $<C_{12}$. The surfactant solutions are particularly used in cosmetic compositions.

11 Claims, No Drawings

(56) References Cited

OTHER PUBLICATIONS

U.S. Appl. No. 14/401,323, now published as US 2015-0141508.
U.S. Appl. No. 14/401,337, now published as US 2015-0141466.
U.S. Appl. No. 14/401,354, now published as US 2015-0125415.
U.S. Appl. No. 14/402,954, now published as US 2015-0140048.
U.S. Appl. No. 14/899,835, now published as US 2016/0143828.
U.S. Appl. No. 14/402,996, now published as US 2015-0164755.
U.S. Appl. No. 14/403,049, now published as US 2015-0150767.
U.S. Appl. No. 14/403,072, now published as US 2015-0164756.
U.S. Appl. No. 14/401,796, now published as US 2015-0126424.
U.S. Appl. No. 14/439,052, now published as US 2015-0320037.
U.S. Appl. No. 14/785,599, now published as US 2016-0074310.
U.S. Appl. No. 14/901,090, now published as US 2016-0136072.
U.S. Appl. No. 15/037,172, now published as US 2016-0272666.
U.S. Appl. No. 15/100,165, now published as US 2017-0002297.
U.S. Appl. No. 15/039,970, now published as US 2016-0361243.
U.S. Appl. No. 15/100,039, now published as US 2017-0000710.
U.S. Appl. No. 15/035,120, now published as US 2016-0243014.
U.S. Appl. No. 15/526,464, now published as US 2017-0305838.
U.S. Appl. No. 15/120,097, now published as US 2017-0071199.
U.S. Appl. No. 15/120,103, now published as US 2017-0055524.
U.S. Appl. No. 15/123,065, now published as US 2017-0101606.
U.S. Appl. No. 15/123,143, now published as US 2017-0218293.
U.S. Appl. No. 15/307,205, now published as US 2017-0044434.
U.S. Appl. No. 15/515,324, now published as US 2017-0265477.
U.S. Appl. No. 15/511,987, now published as US 2017-0292062.
U.S. Appl. No. 14/662,564.
U.S. Appl. No. 14/677,500.
U.S. Appl. No. 14/491,615.
U.S. Appl. No. 15/562,852.
U.S. Appl. No. 15/744,645.
International Search Report for PCT/EP2013/061100, dated Jul. 15, 2014.
Machine translation of WO 96/10386, Apr. 11, 1996.

\* cited by examiner

USE OF N-METHYL-N-ACYLGLUCAMINES AS THICKENING AGENTS IN SURFACTANT SOLUTIONS

The invention relates to the use of N-methyl-N-acylglucamines as thickeners in surfactant solutions and to cosmetic compositions containing said surfactant solutions.

High requirements are imposed on cosmetic products. They should be of clear appearance, must be toxicologically and ecotoxicologically harmless, produce a pleasant sensation on the skin and have excellent rheological behavior that remains constant over a wide range of pH.

Multi-component systems containing water or solvents, such as emulsions or suspensions, are often adjusted to higher viscosities, or thickened, for economic reasons, for practical reasons or for reasons of stability.

Thus, for example increasing the viscosity of the external or internal phase of emulsions or suspensions may greatly prolong the time to separation of the components of such a system, which is reflected in an increase in storage life. With many products, increasing their viscosity also improves their capacity for uniform spreading, especially on uneven surfaces.

The more uniform distribution and longer time of action thus increase the efficacy. In addition to the aforementioned practical advantages, the high viscosity of such preparations also offers further advantages in production, packaging, filling and storage and in transport.

A great many different systems for adjusting the rheological properties of aqueous or solvent-containing systems, emulsions or suspensions are described in the technical literature. For example, cellulose ethers and other cellulose derivatives (e.g. carboxymethylcellulose, hydroxyethylcellulose), gelatin, starch and starch derivatives, sodium alginates, fatty acid polyethylene glycol esters, agar-agar, tragacanth or dextrins are known. Various materials are used as synthetic polymers, for example polyvinyl alcohols, polyacrylamides, polyacrylic acid and various salts of polyacrylic acid, polyvinylpyrrolidone, polyvinyl methyl ethers, polyethylene oxides, copolymers of maleic acid anhydride and vinyl methyl ethers, and various mixtures and copolymers of the aforementioned compounds.

However, the aforementioned compounds show various disadvantages in use. For example, the cellulose derivatives or generally the materials based on natural raw materials and the resultant formulations are very susceptible to bacteria. In practical application, they are generally characterized by the formation of unpleasant, "ropy" gels. In the presence of water, fatty acid polyethylene glycol esters tend to undergo hydrolysis, and the resultant insoluble fatty acids cause undesirable clouding. Thickeners of natural origin (e.g. agar-agar or tragacanth) have a greatly fluctuating composition, depending on their origin.

In EP-A 0 285 768, N-polyhydroxyalkyl fatty acid amides are proposed as thickeners for liquid aqueous surfactant systems. In the practical examples of this document, N-methyl coconut fatty acid glucamide is used as thickener in an ether sulfate-paraffin sulfonate mixed system.

Although good results are already achieved with such a system, there is still room for improvement, for example with respect to thickener performance. The task was therefore to provide thickeners for surfactant systems that display higher thickener performance relative to the known systems.

It was found that certain N-methyl-N-acylglucamines are particularly suitable as thickeners for surfactant systems that contain alkyl ether sulfates or alkyl sulfates, especially in combination with betaines.

The invention therefore relates to the use of N-methyl-N-acylglucamines as thickeners in an aqueous surfactant system containing at least one alkyl ether sulfate and/or at least one alkyl sulfate, wherein at least 60 wt % of said N-methyl-N-acylglucamines have a $C_{12}$-, $C_{14}$- or unsaturated $C_{18}$-acyl group and the content of N-methyl-N-acylglucamines with an acyl group shorter than $C_{12}$ is below 5%.

N-methyl-N-acylglucamines used according to the invention with $C_{12}$- and $C_{14}$-acyl groups and fatty acid ether sulfates or fatty acid sulfates are known from WO 92/06158 or WO 92/06162 for use in rinsing and cleaning agents. However, particular suitability of the glucamide/surfactant combinations according to the invention as thickeners especially for cosmetic compositions cannot be inferred from that.

The N-methyl-N-acylglucamines used according to the invention, also known as N-methyl-N-1-deoxysorbityl fatty acid amides, contain at least 60 wt % of N-methyl-N-acylglucamines that contain a $C_{12}$-, $C_{14}$- or an unsaturated $C_{18}$-acyl group (called "$C_{12/18}$-N-methyl-N-acylglucamines" hereinafter) and simultaneously contain less than 5 wt % of N-methyl-N-acylglucamines that contain a fatty acid residue <$C_{12}$. The following wt % data are relative to the total amount of N-methyl-N-acylglucamines (100 wt %).

Saturated N-methyl-N-acylglucamines of formula (I), where the acyl residue $R^aCO$ is derived from lauric acid, myristic acid, oleic acid, linoleic acid or linolenic acid, are especially preferred as component a):

Formula (I)

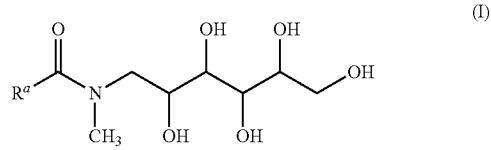

The proportion of N-methyl-N-acylglucamines that contain a $C_{12}$-$C_{14}$- or an unsaturated $C_{18}$-acyl group is at least 60, preferably 70, especially preferably 80 and quite especially preferably 90 wt %.

In addition, the N-methyl-N-acylglucamines used as thickeners according to the invention contain small proportions of N-methyl-N-acylglucamines derived from short-chain and/or long-chain fatty acids, especially those that contain $C_1$-$C_4$-acyl, $C_6$-, $C_8$-, $C_{10}$-, $C_{16}$-, $C_{18}$- and/or $C_{20}$-acyl groups.

The proportion of N-methyl-N-acylglucamines that contain an acyl group <$C_{12}$ is less than 5, preferably 3, especially preferably 2, wt %.

The proportion of N-methyl-N-acylglucamines that contain an unsaturated $C_{18}$-acyl group is preferably at least 8, especially preferably at least 15, wt %.

Especially preferably, the proportion of N-methyl-N-acylglucamines that contain a $C_{12}$-, $C_{14}$- or an unsaturated $C_{18}$-acyl group is at least 70 wt % and the proportion of N-methyl-N-acylglucamines that contain an acyl group <$C_{12}$ is less than 3%.

Especially preferably, the proportion of N-methyl-N-acylglucamines that contain a $C_{12}$-, $C_{14}$- or an unsaturated $C_{18}$-acyl group is at least 80 wt % and the proportion of N-methyl-N-acylglucamines that contain an acyl group <$C_{12}$ is less than 2%.

In another embodiment, the proportion of N-methyl-N-acylglucamines that contain a $C_{12}$- or a $C_{14}$-acyl group is at least 90 wt % and the proportion of N-methyl-N-acylglucamines that contain an acyl group $<C_{12}$ is less than 2%.

In another preferred embodiment, the proportion of N-methyl-N-acylglucamines that contain a $C_{12}$-, $C_{14}$- or an unsaturated $C_{18}$-acyl group is at least 60 wt % and the proportion of N-methyl-N-acylglucamines that contain an acyl group $<C_{12}$ is less than 5%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 60 wt % and the proportion of N-methyl-N-acylglucamines that contain an acyl group $<C_{12}$ is less than 5%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 60 wt % and the proportion of N-methyl-N-acylglucamines that contain an acyl group $<C_{12}$ is less than 3%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 60 wt % and the proportion of N-methyl-N-acylglucamines that contain an acyl group $<C_{12}$ is less than 3%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 60 wt % and the proportion of N-methyl-N-acylglucamines that contain an acyl group $<C_{12}$ is less than 2%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 60 wt % and the proportion of N-methyl-N-acylglucamines that contain an acyl group $<C_{12}$ is less than 2%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 70 wt % and the proportion of N-methyl-N-acylglucamines that contain an acyl group $<C_{12}$ is less than 5%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 70 wt % and the proportion of N-methyl-N-acylglucamines that contain an acyl group $<C_{12}$ is less than 5%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 70 wt % and the proportion of N-methyl-N-acylglucamines that contain an acyl group $<C_{12}$ is less than 3%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 70 wt % and the proportion of N-methyl-N-acylglucamines that contain an acyl group $<C_{12}$ is less than 3%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 70 wt % and the proportion of N-methyl-N-acylglucamines that contain an acyl group $<C_{12}$ is less than 2%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 70 wt % and the proportion of N-methyl-N-acylglucamines that contain an acyl group $<C_{12}$ is less than 2%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 80 wt % and the proportion of N-methyl-N-acylglucamines that contain an acyl group $<C_{12}$ is less than 5%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 80 wt % and the proportion of N-methyl-N-acylglucamines that contain an acyl group $<C_{12}$ is less than 5%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 80 wt % and the proportion of N-methyl-N-acylglucamines that contain an acyl group $<C_{12}$ is less than 3%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 80 wt % and the proportion of N-methyl-N-acylglucamines that contain an acyl group $<C_{12}$ is less than 3%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 80 wt % and the proportion of N-methyl-N-acylglucamines that contain an acyl group $<C_{12}$ is less than 2%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 80 wt % and the proportion of N-methyl-N-acylglucamines that contain an acyl group $<C_{12}$ is less than 2%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 90 wt % and the proportion of N-methyl-N-acylglucamines that contain an acyl group $<C_{12}$ is less than 5%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 90 wt % and the proportion of N-methyl-N-acylglucamines that contain an acyl group $<C_{12}$ is less than 5%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 90 wt % and the proportion of N-methyl-N-acylglucamines that contain an acyl group $<C_{12}$ is less than 3%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 90 wt % and the proportion of N-methyl-N-acylglucamines that contain an acyl group $<C_{12}$ is less than 3%, wherein the proportion the proportion of N-methyl-N-acylglucamines that contain an unsaturated $C_{18}$-acyl group is at least 15 wt %.

In another preferred embodiment, the proportion of N-methyl-N-acylglucamines that contain a $C_{12}$-, $C_{14}$- or an unsaturated $C_{18}$-acyl group is at least 90 wt % and the proportion of N-methyl-N-acylglucamines that contain an acyl group $<C_{12}$ is less than 2%, wherein the proportion the proportion of N-methyl-N-acylglucamines that contain an unsaturated $C_{18}$-acyl group is at least 8 wt %.

In another preferred embodiment, the proportion of N-methyl-N-acylglucamines that contain a $C_{12}$-, $C_{14}$- or an unsaturated $C_{18}$-acyl group is at least 90 wt % and the proportion of N-methyl-N-acylglucamines that contain an acyl group $<C_{12}$ is less than 2%, wherein the proportion the proportion of N-methyl-N-acylglucamines that contain an unsaturated $C_{18}$-acyl group is at least 15 wt %.

The N-methyl-N-acylglucamines may, as described in EP-A 0 550 637 B1 and EP-A 0 285 768, be produced by reaction of the corresponding fatty acid esters or fatty acid ester mixtures with N-methylglucamine in the presence of a solvent that has hydroxyl groups or alkoxy groups. Suitable solvents are for example $C_1$-$C_4$ monohydric alcohols, ethylene glycol, propylene glycol, glycerol and alkoxylated alcohols. 1,2-Propylene glycol is preferred. N-methyl-glucamine may, as also described in EP 0 550 637 A1, be produced by reductive amination of glucose with methylamine. Suitable fatty acid esters that are converted with the N-methylglucamines to glucamides according to the invention are in general the methyl esters that are obtained by transesterification from natural fats and oils, for example the triglycerides.

Fatty acid residues with one or more double bonds are to be understood as unsaturated $C_{18}$-acyl groups in the sense of the invention. In this case residues that are derived from oleic acid, linoleic and linolenic acid are preferred.

The aqueous surfactant solutions contain one or more anionic surfactants from the group of the alkyl sulfates and alkyl ether sulfates.

Preferred alkyl sulfates are the $C_8$-$C_{20}$-alkyl sulfates, especially the linear $C_8$-$C_{20}$-alkyl sulfates in the form of their sodium, potassium or ammonium salts. Examples of alkyl sulfates are lauryl sulfate, coconut alkyl sulfate and tallow alkyl sulfate. Lauryl sulfate is especially preferred.

Preferred alkyl ether sulfates are the $C_8$-$C_{20}$-alkyl ether sulfates, and the linear $C_8$-$C_{20}$-alkyl ether sulfates are especially preferred, especially the alkyl glycol ether sulfates derived from the ethoxylated fatty alcohols, in the form of their sodium, potassium or ammonium salts. Examples of alkyl ether sulfates are lauryl ether sulfate, coconut alkyl ether sulfate and tallow alkyl ether sulfate. Examples of glycol ether sulfates are lauryl-triethylene glycol ether sulfate, coconut alkyltriethylene glycol ether sulfate and tallow alkylhexaethylene glycol ether sulfate. Lauryl glycol ether sulfate is especially preferred, for example, lauryl diethylene glycol ether sulfate or lauryl triethylene glycol ether sulfate, especially in the form of the sodium salts.

The aqueous surfactant solutions preferably contain a betaine surfactant along with the at least one anionic surfactant.

Betaine surfactants contain, in the same molecule, a cationic group, especially an ammonium group, and an anionic group, which may be a carboxylate group, sulfate group or sulfonate group. Suitable betaines are alkyl betaines such as coconut betaine or fatty acid alkylamidopropyl betaines, for example coconut acylamidopropyldimethyl betaine, $C_{12}$-$C_{18}$-dimethylaminohexanoate or $C_{10}$-$C_{18}$-acylamidopropane-dimethyl betaines.

In a preferred embodiment of the invention, the aqueous surfactant solutions contain one or more amidopropyl betaines of formula (II),

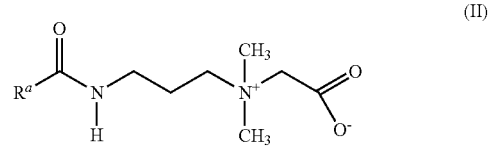

(II)

in which $R^a$ is a linear or branched saturated $C_7$-$C_{21}$ alkyl group or a linear or branched monounsaturated or polyunsaturated $C_7$-$C_{21}$ alkenyl group.

In another preferred embodiment of the invention the surfactant solutions contain one or more betaines of formula (III),

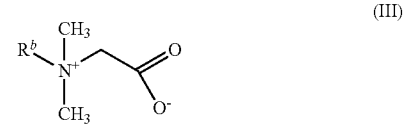

(III)

in which $R^b$ is a linear or branched saturated $C_8$-$C_{22}$ alkyl group or a linear or branched monounsaturated or polyunsaturated $C_8$-$C_{22}$ alkenyl group.

In another preferred embodiment of the invention, the surfactant solutions contain one or more sulfobetaines of formula (IV),

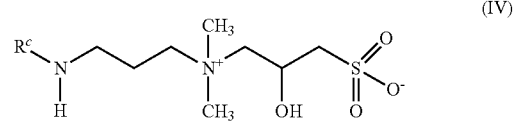

(IV)

in which $R^c$ is a linear or branched saturated $C_8$-$C_{22}$ alkyl group or a linear or branched monounsaturated or polyunsaturated $C_8$-$C_{22}$ alkenyl group.

Especially preferably, the surfactant solutions contain one or more betaine surfactants selected from the group of compounds consisting of the amidopropyl betaines of formula (II), the betaines of formula (III) and the sulfobetaines of formula (IV).

In an especially preferred embodiment of the invention the surfactant solutions contain one or more betaine surfactants selected from the amidopropyl betaines of formula (II).

In another especially preferred embodiment of the invention the surfactant solutions contain one or more betaine surfactants selected from the betaines of formula (III).

In another especially preferred embodiment of the invention the surfactant solutions contain one or more betaine surfactants selected from the sulfobetaines of formula (IV).

The residue $R^a$ in the one or more amidopropyl betaines of formula (II) is preferably a linear or branched saturated $C_7$-$C_{17}$ alkyl group. Among the linear and branched saturated alkyl groups $R^a$, the linear saturated alkyl groups are preferred.

Especially preferably, the amidopropyl betaines of formula (II) are cocoamidopropyl betaines.

The residue $R^b$ in the one or more betaines of formula (III) is preferably a linear or branched saturated $C_8$-$C_{18}$-alkyl group and especially preferably a linear or branched saturated $C_{12}$-$C_{18}$-alkyl group. Among the linear and branched saturated alkyl groups $R^b$, the linear saturated alkyl groups are preferred.

The residue $R^c$ in the one or more sulfobetaines of formula (IV) is preferably a linear or branched saturated $C_8$-$C_{18}$ alkyl group and especially preferably a linear or branched saturated $C_{12}$-$C_{18}$ alkyl group. Among the linear and branched saturated alkyl groups $R^c$, the linear saturated alkyl groups are preferred.

Especially preferably, the aqueous surfactant solutions contain amidopropyl betaines of formula (II) and/or alkyl betaines of formula (III).

The invention further relates to a method of thickening an aqueous surfactant solution, containing at least one alkyl ether sulfate and/or at least one alkyl sulfate, wherein an N-methyl-N-acylglucamine mixture according to the invention is added to the aqueous surfactant solution. Preferred embodiments are those described above.

The invention also relates to cosmetic compositions, containing
(a) one or more N-methyl-N-acylglucamines that contain at least 60 wt % of N-methyl-N-acylglucamines with a $C_{12}$-, $C_{14}$- or an unsaturated $C_{18}$-acyl group (called "$C_{12/18}$-N-methyl-N-acylglucamines" hereinafter) and simultaneously less than 5 wt % of N-methyl-N-acylglucamines with an acyl group <$C_{12}$,
(b) one or more anionic surfactants from the group of the alkyl ether sulfates and alkyl sulfates as component (B),
(c) optionally betaine surfactants as component (C),
(d) optionally further surfactants as component (D),
(e) water as component (E) and
(f) optionally further additives such as preservatives, odorants, colorants, and refatting agents as component (F).

Preferred components a), b) and c) correspond to those mentioned above.

In general the compositions contain
(a) 0.1 to 10.0 wt %, preferably 1 to 5 wt % of component (A),
(b) 0.1 to 15 wt %, preferably 1 to 10 wt % of component (B),
(c) 0 to 10 wt %, preferably 1 to 8 wt % of component (C),
(d) 0 to 10 wt %, preferably 1 to 6 wt % of component (D),
(e) 45 to 99.8 wt %, preferably 75 to 95 wt % of component (E) and
(f) 0 to 10 wt %, preferably 0.1 to 5 wt % of component (F).

The cosmetic compositions according to the invention preferably contain the alkyl sulfates and/or alkyl ether sulfates and betaine surfactants described above.

Optional further surfactants (D) may be cationic, nonionic or amphoteric surfactants.

Suitable cationic surfactants are for example substituted or unsubstituted, linear or branched quaternary ammonium salts of the type $R^1N(CH_3)_3X$, $R^1R^2N(CH_3)_2X$, $R^1R^2R^3N(CH_3)X$ or $R^1R^2R^3R^4NX$. The residues $R^1$, $R^2$, $R^3$ and $R^4$ may preferably be, independently of one another, unsubstituted alkyl with a chain length between 8 and 24 carbon atoms, especially between 10 and 18 carbon atoms, hydroxyalkyl with 1 to 4 carbon atoms, phenyl, $C_2$- to $C_{18}$-alkenyl, $C_7$- to $C_{24}$-aralkyl, $(C_2H_4O)_xH$, wherein x denotes from 1 to 3, one or more ester groups containing alkyl residues or cyclic quaternary ammonium salts. X is a suitable anion. $(C_8$-$C_{22})$-alkyltrimethylammonium chloride or bromide are preferred, cetyltrimethyl-ammonium chloride or bromide, di($C_8$-$C_{22}$)-alkyldimethylammonium chloride or bromide, $(C_8$-$C_{22})$-alkyldimethylbenzylammonium chloride or bromide, $(C_8$-$C_{22})$-alkyl-dimethylhydroxyethyl-ammonium chloride, phosphate, sulfate, lactate are especially preferred, and distearyldimethylammonium chloride, di($C_8$-$C_{22}$)-alkylamidopropyltrimethylammonium chloride and methosulfate are especially preferred.

The amount of the cationic surfactants in the compositions according to the invention may be up to 10 wt %, relative to the total weight of the finished compositions.

For example the following compounds may come into consideration as nonionic surfactants:

Polyethylene-, polypropylene- and polybutylene-oxide condensates of alkylphenols. These compounds comprise the condensation products of alkylphenols with a $C_6$- to $C_{20}$-alkyl group, which may be either linear or branched, with alkene oxides. These surfactants are designated as alkylphenol alkoxylates, e.g. alkylphenol ethoxylates.

Condensation products of aliphatic alcohols with 1 to 25 mol ethylene oxide. The alkyl or alkenyl chain of the aliphatic alcohols may be linear or branched, primary or secondary, and generally contains 8 to 22 carbon atoms. The condensation products of $C_{10}$ to $C_{20}$ alcohols with 2 to 18 mol ethylene oxide per mol of alcohol are especially preferred. The alcohol ethoxylates may have a narrow ("Narrow Range Ethoxylates") or a broad homologous distribution of the ethylene oxide ("Broad Range Ethoxylates"). Examples of commercially available nonionic surfactants of this type are Tergitol® 15-S-9 (condensation product of a linear secondary $C_{11}$-$C_{15}$ alcohol with 9 mol ethylene oxide), Tergitol® 24-L-NMW (condensation product of a linear primary $C_{12}$-$C_{14}$ alcohol with 6 mol ethylene oxide with narrow molecular weight distribution). This product class also includes the Genapol® brands from Clariant.

Condensation products of ethylene oxide with a hydrophobic basis, formed by condensation of propylene oxide with propylene glycol. The hydrophobic moiety of these compounds preferably has a molecular weight between 1500 and 1800. Addition of ethylene oxide to this hydrophobic moiety leads to an improvement in water solubility. The product is liquid up to a polyoxyethylene content of approx. 50% of the total weight of the condensation product, which corresponds to condensation with up to approx. 40 mol ethylene oxide. Commercially available examples in this product class are the Pluronic® brands from BASF and the Genapol® PF brands from Clariant.

Condensation products of ethylene oxide with a reaction product of propylene oxide and ethylenediamine. The hydrophobic unit of these compounds consists of the reaction product of ethylenediamine with excess propylene oxide and generally has a molecular weight from 2500 to 3000. Ethylene oxide is added onto this hydrophobic unit up to a content of 40 to 80 wt % of polyoxyethylene and a molecular weight from 5000 to 11000. Commercially available examples from this class of compounds are the Tetronic® brands from BASF and the Genapol® PN brands from Clariant.

Other suitable nonionic surfactants are alkyl- and alkenyloligoglycosides and fatty acid polyglycol esters or fatty amine polyglycol esters with in each case 8 to 20, preferably 12 to 18, carbon atoms in the fatty alkyl residue, alkyloligoglycosides, alkenyloligoglycosides and fatty acid-N-alkylglucamides.

The amount of the nonionic surfactants in the compositions according to the invention may be up to 10 wt %, relative to the total weight of the finished compositions.

Furthermore, the compositions according to the invention may contain amphoteric surfactants. These can be described as derivatives of long-chain secondary or tertiary amines, which have an alkyl group with 8 to 18 carbon atoms and in which another group is substituted with an anionic group, which imparts the water solubility, for instance with a carboxyl, sulfate or sulfonate group. Preferred amphoteric surfactants are N—($C_{12}$-$C_{18}$)-alkyl-β-aminopropionates and N—($C_{12}$-$C_{18}$)-alkyl-β-iminodipropionates as alkali- and mono-, di- and trialkylammonium salts. Other suitable surfactants also include amine oxides. These are oxides of tertiary amines with a long-chain group of from 8 to 18 carbon atoms and two generally short-chain alkyl groups with 1 to 4 carbon atoms. For example the $C_{10}$- to $C_{18}$-alkyldimethylamine oxides, fatty acid amidoalkyl-dimethylamine oxide are preferred in this case.

The amount of the amphoteric surfactants in the compositions according to the invention may be up to 10 wt %, relative to the total weight of the finished compositions.

Aids and additives e) are for example preservatives, odorants, colorants and refatting agents.

Suitable preservatives are those listed in the relevant annex of the European cosmetics legislation, for example phenoxyethanol, benzyl alcohol, parabens, benzoic acid and sorbic acid, and for example 1,3-bis(hydroxymethyl)-5,5-dimethylimidazolidine-2,4-dione (Nipaguard® DMDMH) is particularly suitable.

The amount of the preservatives in the compositions according to the invention is generally from 0.1 to 2.0 wt %, relative to the total weight of the finished compositions.

Individual fragrance compounds, e.g. the synthetic products of the type of the esters, ethers, aldehydes, ketones, alcohols and hydrocarbons, may be used as odorants. Fragrance compounds of the ester type are e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzylsalicylate. The ethers include for example benzylethyl ether, the aldehydes include e.g. the linear alkanals with 8 to 18 carbon atoms, citral, citronellal, citronellyloxyacetaldehyde, hydroxycitronellal, lilial and bourgeonal, the ketones include e.g. the ionones, alpha-isomethylionone and methylcedryl ketone, the alcohols include anethole, citronellol, eugenol, geranion, linalool, phenylethyl alcohol and terpineol, and the hydrocarbons mainly include the terpenes and balsams. Preferably, mixtures of various fragrances are used, which together produce an attractive perfume note.

Natural fragrance mixtures, such as are accessible from plant or animal sources, e.g. pine, citrus, jasmine, lily, rose, or ylang-ylang oil, may also be used as odorants. Essential oils of lower volatility, which are mostly used as flavor components, are also suitable as perfume oils, e.g. sage oil, chamomile oil, clove oil, melissa oil, mint oil, cinnamon leaf oil, lime blossom oil, juniper berry oil, vetiver oil, olibanum oil, galbanum oil and labdanum oil.

The amount of the odorants in the compositions according to the invention is generally from 0 to 2 wt %, relative to the total weight of the finished compositions.

Lanolin and lecithin, nonethoxylated and polyethoxylated or acylated lanolin and lecithin derivatives, polyol fatty acid esters, mono-, di- and triglycerides and/or fatty acid alkanolamides, these latter serving simultaneously as foam stabilizers, may preferably be used, and they are preferably used in amounts from 0.01 to 10.0 wt %, especially preferably from 0.1 to 5.0 wt % and quite especially preferably from 0.5 to 3.0 wt %.

The dyes and pigments contained in the compositions according to the invention, both organic and inorganic dyes, may be selected from the corresponding positive list of the Cosmetics Directive or the EC-List of Cosmetic Colorants. The following are also used advantageously: nacreous pigments, e.g. pearl essence (guanine/hypoxanthine mixed crystals from fish scales) and mother of pearl (ground mussel shells), monocrystalline nacreous pigments such as bismuth oxychloride (BiOCl), layer-substrate pigments, e.g. mica/metal oxide, silver white nacreous pigments made from $TiO_2$, interference pigments ($TiO_2$, different layer thickness), other interference pigments ($Fe_2O_3$) and combination pigments ($TiO_2/Fe_2O_3$, $TiO_2/Cr_2O_3$, $TiO_2$/Berlin blue, $TiO_2$/carmine).

The amount of the dyes and pigments in the compositions according to the invention is generally from 0.01 to 1.0 wt %, relative to the total weight of the finished compositions.

In a preferred embodiment of the invention, the compositions according to the invention are in the form of products for cleaning the hair and skin, such as hair shampoos, shower gels, hand soaps and facial cleansers.

The invention is explained in more detail in the following examples.

EXAMPLES

Examples 1 to 3 and Comparative Examples 1 to 5

The glucamides described below were produced according to EP 0 550 637 from the corresponding fatty acid methyl esters and N-methylglucamine in the presence of 1,2-propylene glycol as solvent and were obtained as a solid consisting of the active substance and 1,2-propylene glycol (all data in wt %).

| Example of production | Methyl ester | Triglyceride | Active substance (%) | 1,2-Propylene-glycol (%) | Melting point (° C.) |
|---|---|---|---|---|---|
| 1 | C12/14 (C12: 70%, C14 30%) | | 90 | 10 | 85 |
| 2 | | Coconut oil (C8: 6%; C 10: 6%; C12: 48%; C14: 20% C16: 10%; C18: 2%, C18' = 8%) | 90 | 10 | 50 |

| Example of production | Methyl ester | Triglyceride | Active substance (%) | 1,2- Propylene- glycol (%) | Melting point (° C.) |
|---|---|---|---|---|---|
| 3 | C8/10 (C8: 60%; C 10: 40%) | | 90 | 10 | 50 |
| 4 | C 16/18 (C16: 60%; C 18: 40%) | | 80 | 20 | 65 |
| 5 | C12/18 unsaturated (C12: 60%, C14: 26%, C16: 4% C18: 1% C18'(oleic acid): 8% C18" = 1% | | 90 | 10 | 70 |
| 6 | C16/18 unsaturated C16: 32% C18: 8% C18' = 52% C18" = 8% | | 80 | 20 | 45 |
| 7 | Coconut methyl ester C8: 6%; C 10: 6%; C12: 48% C14: 20% C16: 10%; C18: 2%, C18' = 8% | | 90 | 10 | 55 |

Surfactant solutions were produced consisting of sodium lauryl ether sulfate [degree of ethoxylation 2 EO] (Genapol LRO liq., Clariant), cocamidopropyl betaine (Genagen CAB 818, Clariant) and sugar surfactants according to the following table and were adjusted to a uniform viscosity of 5000 mPas by adding common salt. The total surfactant content was in each case 12%. The amount of salt required to give a viscosity of 5000 mPas was determined.

| Example | Proportions: sodium lauryl ether sulphate: cocamidopropyl betaine:sugar surfactant | Sugar surfactant | Amount of salt required for 5000 mPas (%) |
|---|---|---|---|
| Example 1 | 6:2:2 | Production example 1 | 1.0 |
| Example 2 | 6:2:2 | Production example 5 | 0.75 |
| Example 3 | 6:2:2 | Production example 6 | 0.80 |
| Comparative example 1 | 6:2:2 | Production example 2 | 1.70 |
| Comparative example 2 | 6:2:2 | Production example 3 | >3 |
| Comparative example 3 | 6:2:2 | Production example 4 | 1.40 |
| Comparative example 4 | 6:2:2 | Lauryl glucoside (Plantacare 1200) | 1.75 |
| Comparative example 5 | 8:2:0 | None, sodium lauryl ether sulfate: | 2.5 |
| Comparative example 6 | 6:2:2 | Production example 7 | 1.3 |

Formulation examples 1, 2 and 3 according to the invention required by far the lowest salt concentrations relative to the comparative examples not according to the invention. This is advantageous with respect to the dermal and mucosal compatibility of the cosmetic formulations. In particular, it can be seen from example 2 that a synergy in thickening develops when glucamides with chain length C12/14 and unsaturated C18 components are combined. In contrast, the products derived from coconut oil and corresponding to EP 0 285 768 (comparative examples 1 and 6) do not possess thickening performance corresponding to examples 1-3. Comparative example 3 shows that the thickening performance of saturated C16/18 glucamides does not match the compositions according to the invention.

The invention claimed is:

1. A method of thickening an aqueous cosmetic surfactant solution for cleaning hair and skin to a viscosity of at least 5000 mPas while comprising 1.0% weight or less of common salt, wherein the aqueous cosmetic surfactant solution contains a betaine surfactant and one or more anionic surfactants selected from the group consisting of alkyl ether sulfates and alkyl sulfates, comprising the step of adding a N-methyl-N-acylglucamine, wherein the N-methyl-N-acylglucamine contains at least 60 wt % of N-methyl-N-acylglucamines with a $C_{12}$-, $C_{14}$- or an unsaturated $C_{18}$-fatty acid residue and simultaneously less than 5 wt % of N-methyl-N-acylglucamines that contain a fatty acid residue $<C_{12}$ and wherein the proportion of N-methyl-N-acylglucamines that contain an unsaturated $C_{18}$-acyl group is at least 8 wt %, to the aqueous surfactant solution.

2. The method as claimed in claim 1, wherein the at least 60 wt % of N-methyl-N-acylglucamines are compounds of formula (I),

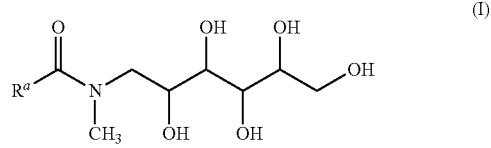

wherein the residue $R^a$ is derived from lauric acid, myristyl acid, oleic acid, linoleic acid or linolenic acid.

3. The method as claimed in claim 1, wherein the proportion of N-methyl-N-acylglucamides that contain a $C_{12}$-, $C_{14}$- or an unsaturated $C_{18}$-acyl group is at least 70 wt %.

4. The method as claimed in claim 1, wherein the proportion of N-methyl-N-acylglucamides that contain a $C_{12}$-, $C_{14}$- or an unsaturated $C_{18}$-acyl group is at least 80 wt %.

5. The method as claimed in claim 1, wherein the proportion of N-methyl-N-acylglucamides that contain a $C_{12}$-, $C_{14}$- or an unsaturated $C_{18}$-acyl group is at least 90 wt %.

6. The method as claimed in claim 1, wherein the proportion of N-methyl-N-acylglucamides that contain an acyl group $<C_{12}$ is less than 3 wt %.

7. The method as claimed in claim 1, wherein the proportion of N-methyl-N-acylglucamides that contain an acyl group $<C_{12}$ is less than 2 wt %.

8. The method as claimed in claim 1, wherein the proportion of N-methyl-N-acylglucamines that contain an unsaturated $C_{18}$-acyl group is at least 15 wt %.

9. The method as claimed in claim 1, wherein the aqueous surfactant solutions contain a linear $C_8$-$C_{20}$-alkyl sulfate and/or a linear $C_8$-$C_{20}$-alkyl ether sulfate.

10. The method as claimed in claim 1, wherein the aqueous surfactant solutions contain lauryl sulfate and/or a lauryl ether sulfate.

11. The method as claimed in claim 1, wherein the aqueous surfactant solutions contain an acylamidopropyl betaine or an alkyl betaine.

* * * * *